(12) United States Patent
Landau

(10) Patent No.: US 6,506,177 B2
(45) Date of Patent: *Jan. 14, 2003

(54) NEEDLE-LESS INJECTION SYSTEM

(76) Inventor: Sergio Landau, 49 S. Peak, Laguna Nigel, CA (US) 92677

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 12 days.

(21) Appl. No.: 09/173,071

(22) Filed: Oct. 14, 1998

(65) Prior Publication Data
US 2002/0151839 A1 Oct. 17, 2002

(51) Int. Cl.7 .............................. A61M 5/30; A61M 5/20
(52) U.S. Cl. ........................................ 604/68; 604/135
(58) Field of Search ............................ 604/68–71, 131, 604/133, 135, 134, 187

(56) References Cited

U.S. PATENT DOCUMENTS

| 4,090,512 A | * | 5/1978 | Doherty et al. | ......... 128/173 H |
| 4,266,541 A |   | 5/1981 | Landau | |
| 4,592,742 A |   | 6/1986 | Landau | |
| 5,080,648 A |   | 1/1992 | D'Antonio | |
| 5,318,522 A |   | 6/1994 | D'Antonio | |
| 5,569,190 A |   | 10/1996 | D'Antonio | |
| 5,743,889 A | * | 4/1998 | Sams | ......................... 604/211 |
| 5,865,795 A | * | 2/1999 | Schiff et al. | .................. 604/70 |
| 5,879,327 A | * | 3/1999 | DeFarges et al. | ............. 604/68 |
| 5,891,085 A | * | 4/1999 | Lilley et al. | ................. 604/68 |
| 5,891,086 A | * | 4/1999 | Weston | |

OTHER PUBLICATIONS

Vitajet Industria e Comércia Ltda. Omnijet sales brochure, 4 pp, Rio de Janeiro, Brazil, undated.

* cited by examiner

Primary Examiner—Michael J. Hayes
(74) Attorney, Agent, or Firm—Terry L. Miller

(57) ABSTRACT

A needle-less hypodermic jet injection system includes a hand-held injector, and an energizing or cocking unit for use with the injector to prepare it for administering an injection. The hand-held unit includes a cartridge which provides a cylinder of liquid medication to be injected, an injection orifice, and an injection piston forceful movement of which causes an injection jet of medication to be expelled from the orifice. A power unit of the injector provides for forceful movement of the injection piston when a trigger is actuated. After being used to effect an injection, the injector is interfaced with an energizer unit which cocks the power unit preparatory to the next injection.

23 Claims, 7 Drawing Sheets

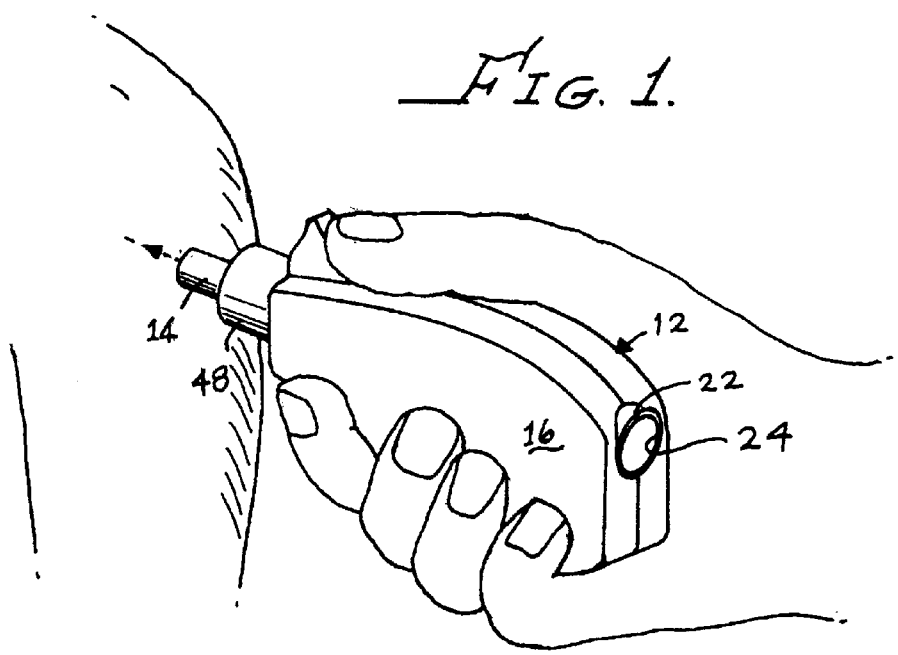
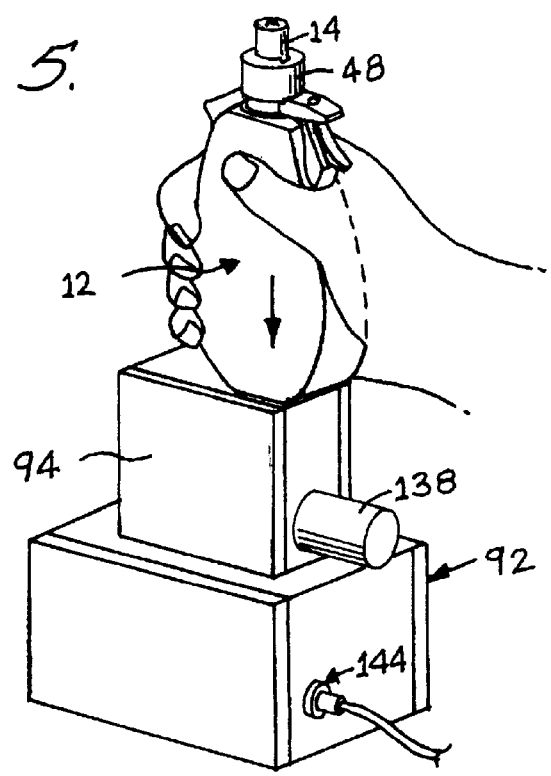

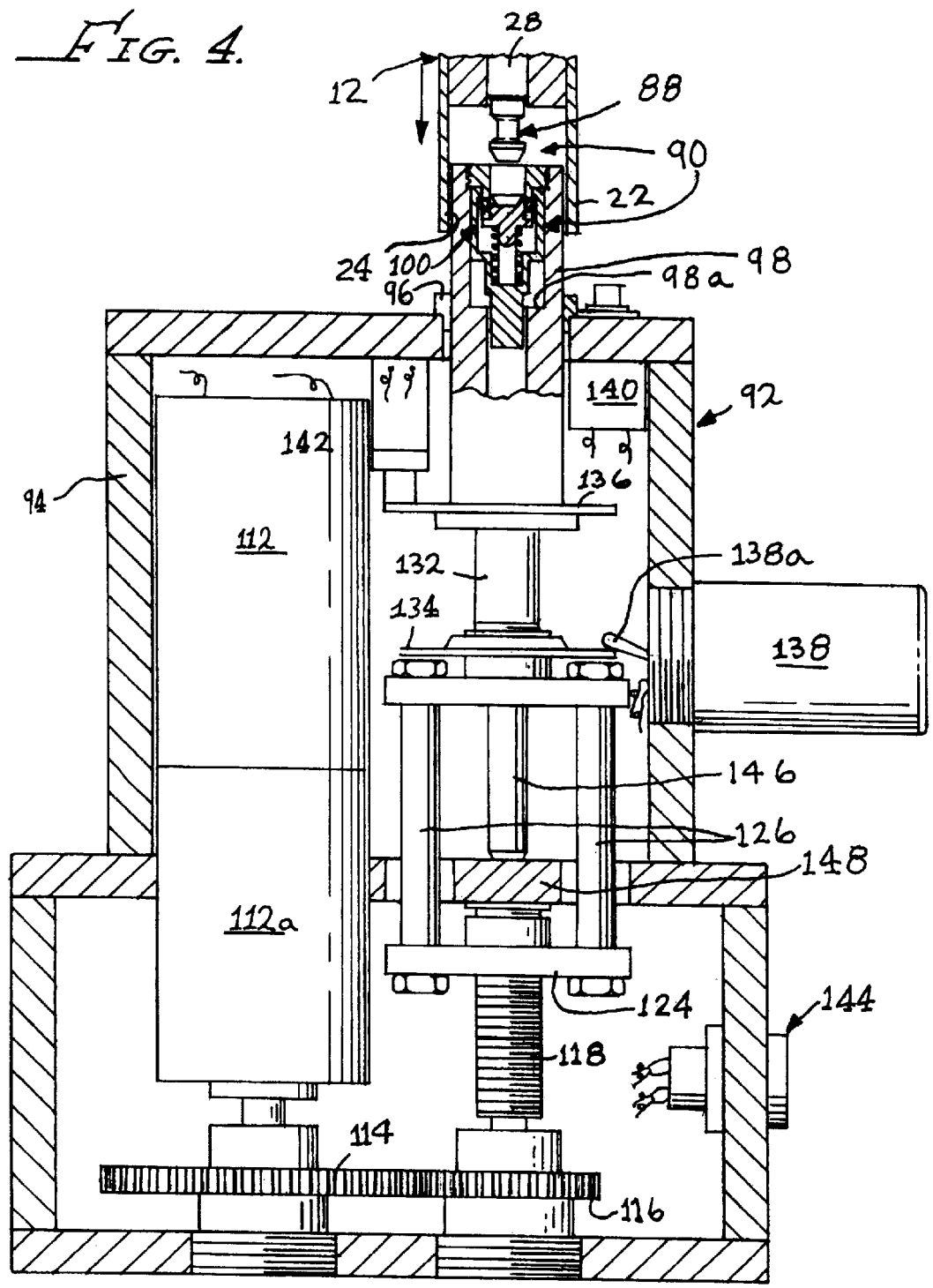

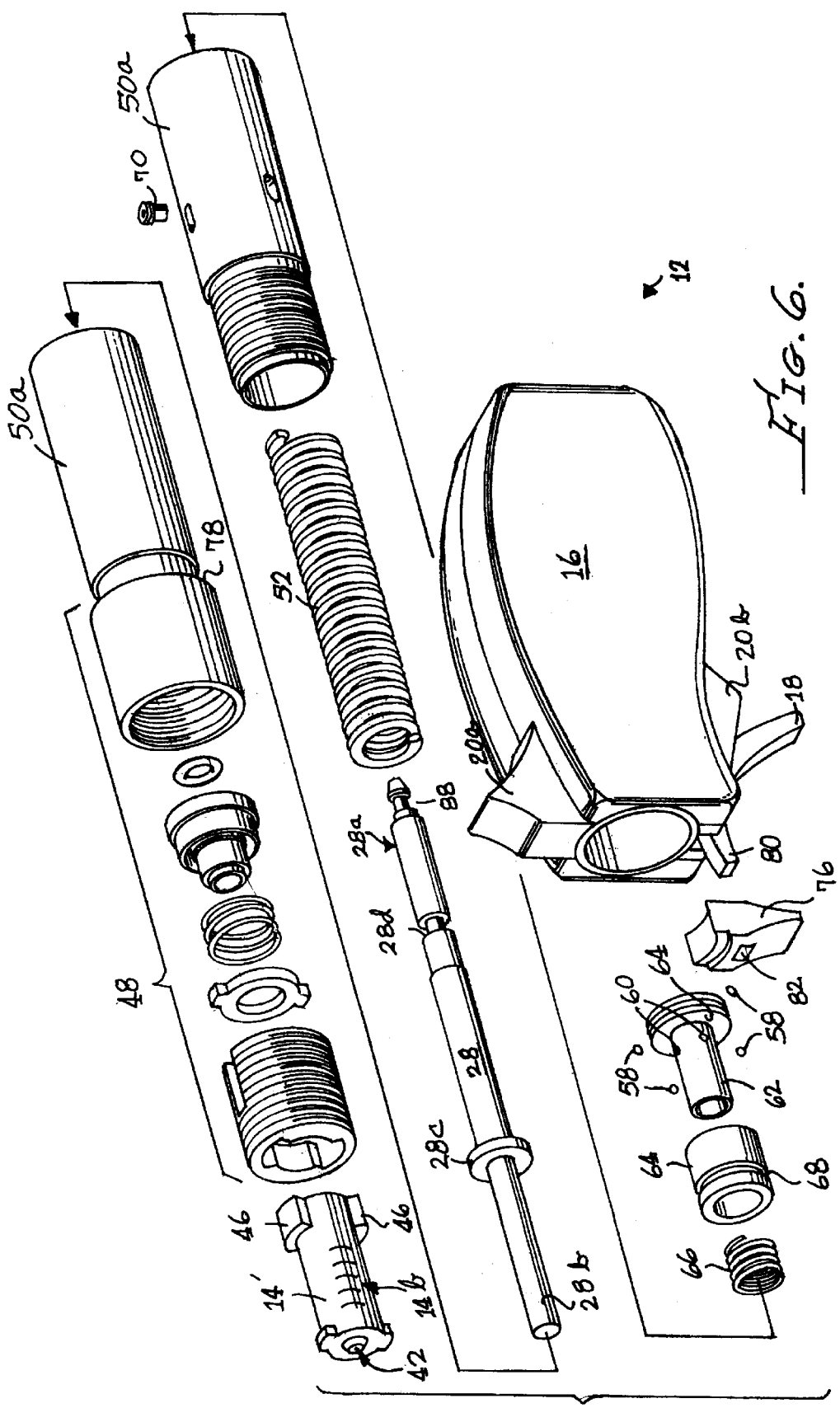

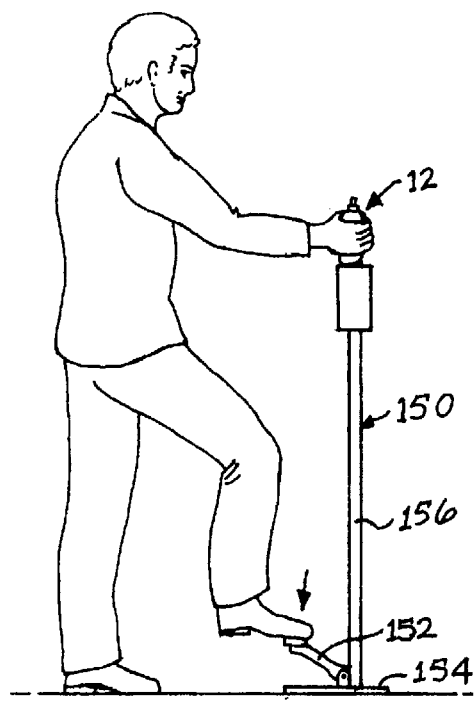
FIG. 7.
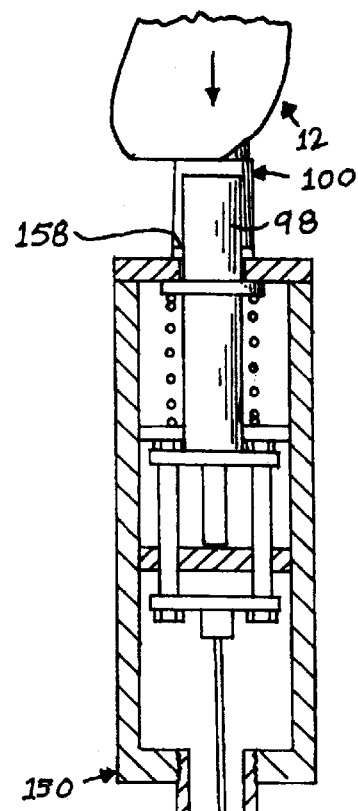
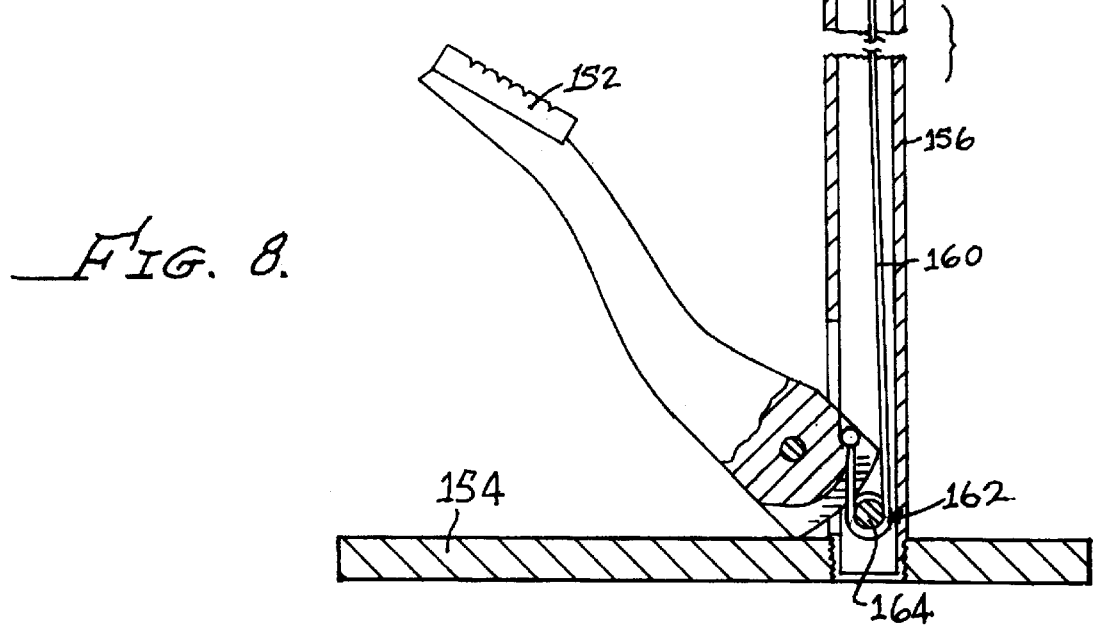
FIG. 8.

NEEDLE-LESS INJECTION SYSTEM

BACKGROUND OF THE INVENTION

1. Field of the Invention

The present invention relates generally to a needle-less or needle-free hypodermic injection device, and particularly to such an injection device with a hand-held injector having a power unit which is pre-energized for the user of the device. A user of the hand-held injector device may pre-energize the power unit of the injector device by interfacing the device with a powered docking station. This powered docking station has a servo drive mechanism cooperating with the power unit to pre-energize it. Alternatively, the injection device may be pre-energized by use of a manual mechanism which employs the application of power provided by a human. For example, a human may step on a pedal of the manual pre-energizing mechanism in order to pre-energize the power unit of the hand-held injector.

The present invention also relates to a pre-filled, needle-free injection cartridge for use on such an injection device and which has features which prevent its unauthorized use for more than one injection.

2. Related Technology

Needle-less or needle-free hypodermic jet injection devices have been in commercial use for over 40 years. Initially hypodermic jet injectors were invented to expedite the process of injecting multiple patients in situations requiring that many injections be given in a short time, such as in a mass vaccination campaigns requiring numerous individuals to be injected with the same vaccine in a short time. In such uses, the same device was used to inject people serially, one person after another, so that a great number of people could be injected in a short time. In other words, such devices found wide application in mass vaccination and mass inoculation campaigns, and in the military, for example, to inoculate recruits. The related technology includes inventions such as: Ismach, U.S. Pat. No. 3,057, 349; Isobe, U.S. Pat. No. 3,526,225; Mizzy, U.S. Pat. No. 3,859,996; and Landau, U.S. Pat. No. 4,266,541.

These inventions and devices for multiple use with many individuals are no longer considered safe. That is, with the wide-spread presence of HIV and Hepatitis B in the general population, the possibility of reflux of blood or body fluids into such an injection device, and subsequent the passing of virus or microorganisms to another individual who later receives an injection from the device clearly makes the risk of their use too great.

However, needle-less hypodermic jet injection devices for multiple use are still considered a safe and reliable means of delivery of certain medications, provided that all parts in contact with the fluid path are disposed of after each injection. That is, for devices that are meant to inject medication to different people, if the nozzle tip touches the patients' skin, it is believed today by public health organizations that the possibility of transferring viruses such as HIV and Hepatitis B from one patient to another exists and may be significant. Further, it is believed that replacing only the nozzle tip after each injection is not sufficient to guarantee complete elimination of cross contamination between patients, because particles of blood or body fluid refluxed during the injection may carry viruses or pathogens to the dose chamber of the device. Therefore, this contamination of the device may contaminate the following medication dose to be injected in the next patient.

Accordingly, in case the same needle-less device is used on different patients, the only "absolute" and acceptable methods to completely avoid cross contamination of diseases are either: a) sterilizing all parts in contact with the dose medication path after each injection, or; b) disposing of all parts in contact with the dose medication path after each injection. The first alternative is too time consuming, and is not practical in today's health care industry because of cost considerations. The second alternative has also not proven to be cost effective for most vaccines and drugs commercially available in the marketplace and based on current technology.

On the other hand, there are needle-less injection devices that are meant to be used by a single patient in therapies that require frequent hypodermic injections of certain drugs to the same patient repeatedly. In other words, the hypodermic jet injection device is used repeatedly, but always on the same patient. Among these frequent, repetitive, and long term injectable drugs are insulin, human growth hormones, interferon for cancer treatment, drugs for migraine headaches, allergy reduction compounds, drugs for male erection dysfunction, injectable birth control drugs, and many others. Since these hypodermic injectable therapies are long term (i.e., some of them for the entire life of the patient), an individual patient may use a needle-less hypodermic jet injection device for a long period of time. That is, each needle-less hypodermic jet injection device is usually used and owned by only one person, in which case it is not medically justifiable for the parts in contact with each dose of medication to be sterilized or disposed of after each injection.

Another context in which needle-less jet injection devices may find application is in the clinical environment, particularly those in which clinic personnel give a rather large number of injections each day. In such uses, the components defining the dose medication path may be pre-filled with a medication, and after a single injection these components are disposed of. Alternatively, the components defining the dose medication path may he refillable, and may be used only on a single patient, although they are used repeatedly on this one patient. In each case, the needle-less hypodermic jet injection device (or injection power unit) will be used several times during a day's treatment of patients, with the clinic personnel using the disposable or refillable components individually for each patient. It is generally accepted by official health institutions, including the U.S. Food and Drug Administration that if a needle-less hypodermic jet injection device is to be used daily by only one person, the injection head or the parts in contact the medicament dose will have to be cleaned and disinfected only once every 15 days.

The related technology includes some inventions such as: Fudge, U.S. Pat. No. 3,908,651; Lindmayer et al., U.S. Pat. No. 4,342,310; and Landau, U.S. Pat. No. 4,592,742, that describe devices that have a reusable or permanent injection head. These devices however, require the users to periodically disassemble the injection head for the necessary cleaning, unclogging and disinfecting. These procedures are time consuming and require a certain skill from the users.

In order to guarantee sterility, avoid the risk of cross contamination and reduce the user's handling of the drug to be injected, in the recent years the concept of single-use disposable medicament dose has been brought to the needle-less hypodermic jet injection devices. The related technology contains several inventions that describe needle-less devices with disposable single-dose medicament containers or cartridges. Among these inventions are the ones in which the drug is pre-filled and the entire needle-less device is single-use and disposed of after each injection, such as:

Parsons, U.S. Pat. No. 4,913,699; Alchas et al., U.S. Pat. No. 5,334,144; and Weston, WO 95/03844.

Other inventions such as: Landau, U.S. Pat. No. 4,966,581; Dunlop, U.S. Pat. No. 5,062,830; and Edwards, U.S. Pat. No. 5,063,165, disclose devices in which the entire device is disposed of after a single use. These devices adequately meet the safety concerns of preventing the spread of disease, but are unacceptably expensive because of the disposal of the device after a single use.

McKinnon, U.S. Pat. No. 5,312,335, describes a device that comprises a needle-less syringe that may be filled manually by the user, outside the gas-powered unit. McKinnon's needle-less syringe is also designed to be single-use as, once a single injection is over, the syringe has to be necessarily removed from the gas powered unit.

These inventions comprising disposable single-use needle-less hypodermic jet injection devices, or needle-less devices that utilize single-use disposable medicament cartridges, have a number of limitations standing in the way of their wide individual and commercial uses. One of these limitations is the difficulty, time, or expense involved in re-cocking or re-energizing the injection units preparatory to the next injection. Some units require the user to have considerable hand strength in order to manipulate the unit and re-cock it. Others require good eye sight in order to assess when the unit is re-energized with a sufficient level of energy for the next injection to be given.

Some of these conventional needle-less hypodermic jet injection devices make use of hydraulic power to cock the injection device, or to energize the injection device preparatory to making of an injection. Others of these devices make use of an internal spring and cocking or energizing mechanism which is contained within the injection device itself. These devices which have the energizing or cocking mechanism within the injection device are necessarily somewhat larger and heavier than would be the case were the energizing device to be located elsewhere.

SUMMARY OF THE INVENTION

In view of the above, it would be desirable and is an object for this invention to provide a needle-less hypodermic jet injection device which includes a pre-filled, single use injection cartridge.

Another object for this invention is to provide a needle-less hypodermic jet injection system which includes a hand-held injection device or injector part which is pre-energized and carries an injection cartridge with medication cylinder, injection nozzle, and injection ram; and which makes use of a separate component of the system to energize the hand piece injector. Still another object for this invention is to provide such a needle-less hypodermic jet injector device which includes an injection hand piece powering the injection cartridge, and which hand piece is quickly re-energized by interfacing the hand piece with a cocking or energizing mechanism. Additionally, it is an object to provide such a needle-less injection device which allows the hand piece to be re-energized by interfacing the hand piece with, for example, a motor-driven re-energizing mechanism, or with a human-powered (i.e., manually or with a pedal, for example) re-energizing mechanism.

In some respects like the single-use needle-less injection devices, this injection system also utilizes an injection head or cartridge which in the present case is made of materials of relatively low cost and good mechanical performance. Preferably, these components of the injection cartridge are made of thermoplastics. But, unlike the older single-cartridge, multiple-use, multiple-recipient devices, and unlike the single-use devices, this invention provides the design features and elements to allow the injection cartridge to be easily refilled and reused by an authorized user who can refill the injection cartridge with the proper amount of medication for each injection.

On the other hand, unlike the reusable needle-less injection devices which require disassembly, cleaning and disinfecting every 15 days, this invention in one embodiment provides the users with the means to easily, quickly and economically remove the injection cartridge, discard it, and replace it with a new one, every 15 days.

So to, the present invention provides features allowing the injection cartridge in an alternative embodiment to be manufactured as a single-use unit; which cannot easily be refilled and reused by the user who is not authorized to do so.

A needle-less hypodermic jet injection system embodying this invention includes, for example: a hand-held injector carrying an injection cartridge with medication cylinder, injection nozzle, and injection ram; the hand-held injector including a power unit which is pre-energized prior to each injection; and a trigger mechanism allowing the energy stored in the power unit to be released and applied in driving the injection ram to cause the injection; and an energizing mechanism with which the hand-held injector interfaces to either be re-energized automatically or by the application of force and displacement applied by a person.

BRIEF DESCRIPTION OF THE DRAWING FIGURES

FIG. 1 is a fragmentary pictorial view of a hand-held needle-less injector being used to give an injection;

Figure 2:
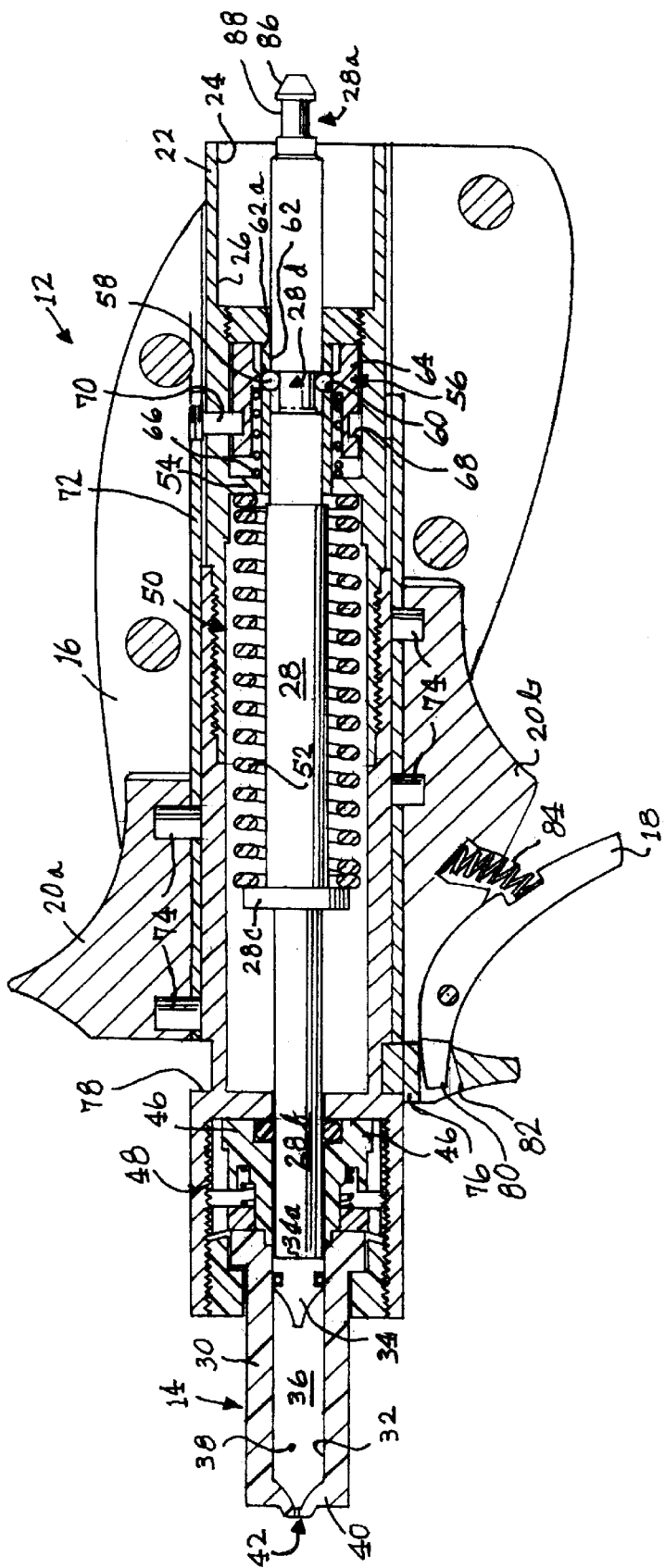
FIG. 2 is a longitudinal view, partially in cross section, of the needle-less injector in its cocked or energized condition and with an injection cylinder installed and filled with medicament preparatory to the giving of an injection.
Figure 3:
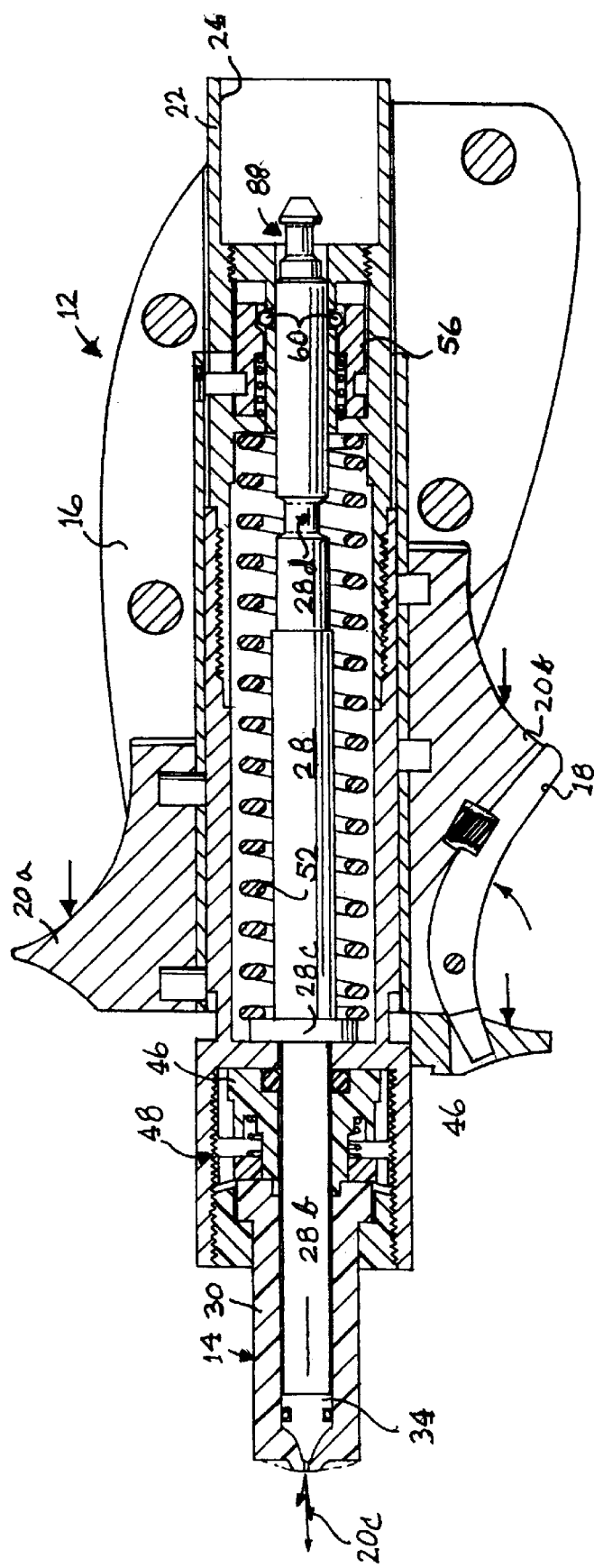
FIG. 3 is a longitudinal view, partially in cross section like that of FIG. 2, but showing the needle-less injector in its un-cocked or de-energized condition which it has after the giving of an injection, and preparatory to re-cocking of this injector.
Figure 4A:
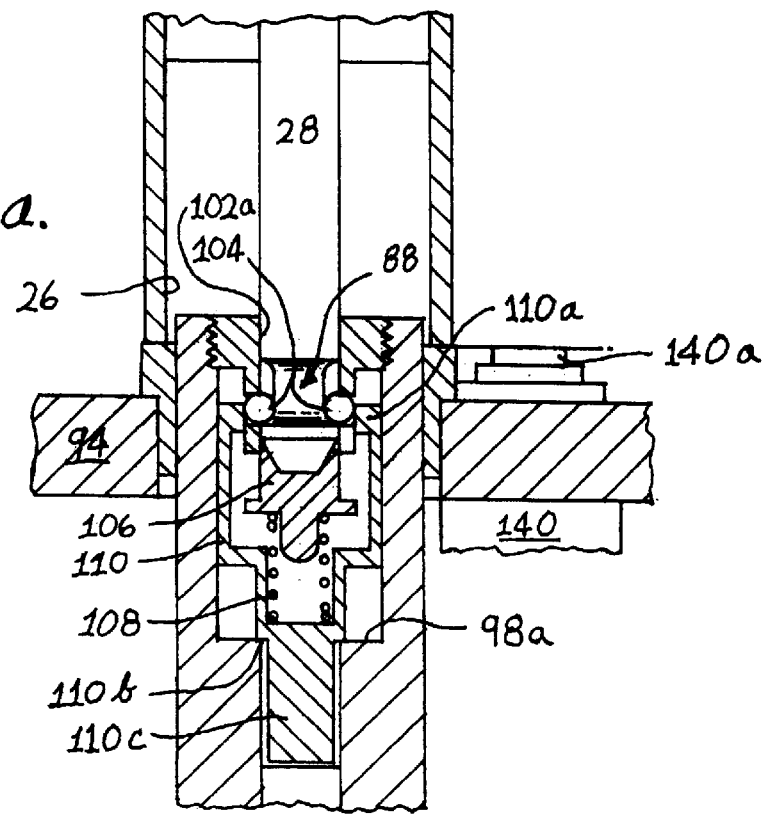
FIG. 4 is a side elevation view, partially in cross section of an automatic energizing unit for use with the hand-held injector seen in FIGS. 1–3.
Figure 4B:
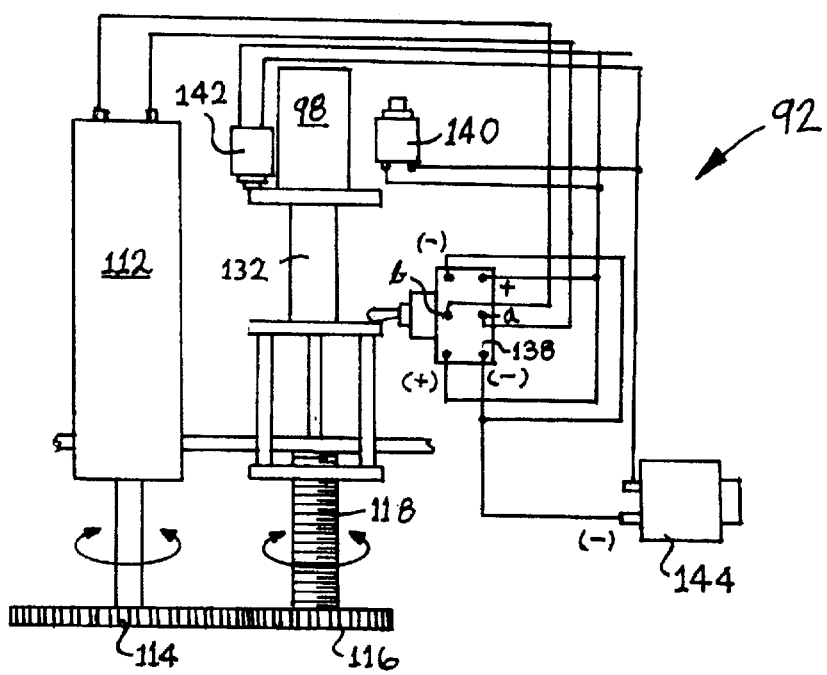

FIG. 4a provides an enlarged fragmentary view of a portion of FIG. 4;

FIG. 4b is a schematic diagram of the electrical connections of the automatic energizing unit seen in FIG. 4;

FIG. 5 is a perspective view of the hand-held needle-less injector installed on the automatic energizing unit seen in FIGS. 4 and 4a;

FIG. 6 is an exploded perspective view of the hand-held needle-less injector, shown exploded to better illustrate features of the components of this injector;

FIG. 7 is a side elevation view of a person using a human-powered energizing device for use with the hand-held needle-less injector seen in FIGS. 1–3; and FIG. 8 is a fragmentary cross sectional view of a portion of the human-powered energizing device seen in FIG. 7.

DETAILED DESCRIPTION OF THE EXEMPLARY PREFERRED EMBODIMENTS OF THE INVENTION

Viewing FIG. 1, a patient 10 is shown being injected with a medication by use of a hand-held needle-less injector 12.

The injector 12 includes an injection cartridge, generally referenced with the numeral 14, and which holds an injection dose of liquid medication (not seen in FIG. 1). This injector 12 also includes an ergonomically shaped body 16, from which projects a safety release 18 for releasing operation using an index finger, and a pair of trigger projections 20a and 20b which are used both to assist in pressing the injection cartridge 14 against the skin of the patient 10 and which when moved forwardly, as is indicated by arrow 20c, results in the injector 12 producing a hypodermic jet injection of the liquid medication held in cartridge 14. At its aft end (i.e., away from the patient 10), the injector 12 includes a cylindrical protrusion 22 defining an opening 24 for a cylindrical bore 26. An end portion 28a of an energizing stem 28 (further described below) is reciprocable in and is shielded in the bore 26. As those ordinarily skilled in the pertinent arts will know, such a hypodermic jet injection results from the forceful expulsion of the liquid medication though a very small orifice to produce a high velocity jet of liquid capable of penetrating the skin without the use of a hypodermic needle. Thus, the injector 12 is needle-free or needle-less.

Turning now to FIGS. 2, 3, and 6 in conjunction, FIG. 2 shows the injector 12 in its energized condition, preparatory to its being used to give an injection as described above. The cartridge 14 includes a cylinder 30 defining a bore 32 in which an injection piston member 34 is movable to cooperatively define a variable-volume chamber 36. The chamber 36 contains a dose of medication, indicated with numeral 38. The bore 32 is substantially closed at its forward end by a wall 40 defining a very fine opening 42. The opening 42 forms an injection orifice through which the medication 38 will be forced at high velocity by forceful forward movement of the injection piston 34. As is seen in the drawing Figures, the injection piston 34 has a bluff back end 34a, which will be seen to be abutted or contacted by a stem 28 of the injector 12. It will also be seen that the injection piston 34 is free at back end surface 34a of any features allowing it to be grasped or engaged to be pulled outwardly of the bore 32. Thus, once the injection piston 34 has been forcefully driven forward toward the wall 40, it is not easily possible (or possible at all) to withdraw the piston 34 once again to the position seen in FIG. 2. Thus, the cartridge 14 will be understood to be a single-use cartridge.

At its aft end, the cylinder 30 includes a pair of oppositely extending lugs 46 by which the cylinder is removably coupled to the injector 12. The injector 12 includes a chuck assembly 48, which accepts and releasably couples with the cylinder 30 by engagement with lugs 42 in the manner of a "bayonet fitting." In other words, the cartridge 14 may be pressed axially into the chuck assembly 48, turned slightly counter-clockwise, and then may be withdrawn from the chuck assembly axially. Similarly, a new cartridge 14 may be assembled to the injector 12 by the reverse of these movements.

As is seen in FIG. 2, the injector includes a power unit, which is indicated by arrowed numeral 50. This power unit has a tubular body, generally indicated with the numeral 50a, which is carried in the housing 16. This power unit 50 also includes a reciprocable energizing stem 28, a forward portion 28b of which forms a ram engaging the piston 34 of the cartridge 14. That is, forward movement of the stem 28 moves the piston 34 forward to expel the medication 38 via orifice 42. In order to store mechanical energy and to forcefully move the stem 28 forward, the power unit 50 includes a strong coil compression spring 52 which at a forward end bears against a collar portion 28c of the stem 28.

Those ordinarily skilled in the pertinent arts will recognize that a number of recognized alternatives may be employed instead of the coil compression spring 52. For example, it has long been recognized in the tool and die art that a nitrogen-charged gas spring (i.e., a piston-cylinder unit holding pressurized nitrogen gas) can be substituted for a coil compression spring. Accordingly, such a nitrogen gas spring may be employed in the injector 12 in substitution for the spring 52. At its aft end, the spring 52 bears against an annular spring seat 54.

In the position seen in FIG. 2, the spring 52 is compressed and stores mechanical energy. The spring 52 is prevented from releasing this energy because the stem 28 is held in the position shown by engagement at a groove 28d with a ball-chuck or ball cluth sear device, indicated with numeral 56. The sear device 56 includes several ball elements 58 which are each held in one of a matching number of apertures 60 of a support sleeve 62. The support sleeve 62 is threadably joined to the body 50a. The balls 58 are prevented from moving outwardly out of engagement with groove 28d by a radially inwardly extending annular collar portion 64a of a trigger collar 64. A coil spring 66 urges the trigger collar 64 into the position seen in FIG. 2 of abutting engagement with a shoulder 62a formed on the support sleeve 62. In order to move the trigger collar 64 axially so that the portion 64a no longer aligns radially with the balls 58, allowing their escape from the groove 28d and release of the stem 28, the trigger collar 64 defines an outer groove 68. A number of radially extending pins 70 (only one of which is seen in FIGS. 2 and 3) engage into the groove 68, and are carried by an outer trigger sleeve 72, which is movable axially along a portion of the outer surface of body 50a. This trigger sleeve 72 similarly carries four outwardly extending pins 74, a pair of which engage into each one of the trigger members 20a and 20b.

As is further seen in FIG. 2, the forward movement of trigger sleeve 72 is blocked by a safety member 76, which is interposed in the position illustrated between a shoulder 78 formed on body 50a and the forward end of sleeve 72. As is illustrated by the arrow associated with safety release 18 the safety member 76 can be moved out of the way of sleeve 72 by a nose portion 80 of this safety release member 18 which is received into a opening 82 of the safety member 76. A spring 84 urges the release 18 and safety member 76 to the safe position shown in FIG. 2.

In view of FIG. 1, it will be understood that a user of the injector 12 releases the safety 18 while pressing the injector against the skin and moving sleeve 72 forward by pressure on trigger portions 20a and 20b, causes the hypodermic jet injection by release of plunger 28.

As FIG. 3 shows, following an injection the plunger 28 is in a forward position, and the spring 52 no longer stores sufficient mechanical energy for an injection, although this spring may still be subject to a considerable pre-load. In order to return the injector 12 to its energized condition, the stem 28 at portion 28a defines a chamfer 86 leading to another groove 88. As will be seen, the groove 88 forms a male part of another sear device (i.e., an energizing sear— generally indicated with numeral 90), which will be further explained below.

Viewing FIGS. 4, 4a and 5 in conjunction, it is seen that an energizing unit 92 includes a housing 94 having an upper abutment surface 96 above which extends a retractable (i.e., reciprocable) power-driven stem 98. FIGS. 4, 4a, and 5 shows that in order to use the energizing unit 92, the injector 12 is placed on the energizer unit by receiving the upwardly extending stem 98 into the bore 24, and abutting an end of the housing 50a with the abutment 96. In this position of the injector 12, FIG. 4a shows that the end portion 28a of stem 28 (i.e., the portion having chamfer 86 and groove 88) enters an assembly 100 which forms the female part of the energizing sear 90. The assembly 100 is carried at the upper extent of stem 98, and includes a support sleeve 102 defining a bore 102a into which the male sear portion of stem 28 is received. The support sleeve 102 carries a number of ball members 104 each captured radially in their respective aperture of the support sleeve 102.

On the one hand, the ball members 104 are captured inwardly in the apertures of the support sleeve 102 by an inner retractable plug member 106 which is urged upwardly be a coil spring 108. On the other hand, the ball members are captured in their respective apertures of sleeve 102 by an outer cup-like sear member 110 which is urged downwardly be the same spring 108. The sear member 110 has an inner annular ridge 110a, which can move into alignment with the balls 104 by downward relative movement of this sear member. When the stem 28 is not present in the support sleeve 102, the balls 104 are in a radially outward position, blocking sear member 110 against such downward relative movement. The cup-like sear member 110 can rest at a shoulder 110b on an internal step 98a of the stem 98 when it does move axially to align ridge 110a with the balls 104. Thus, it is seen that the energizing sear 90 also includes a ball-clutch, as described above.

Accordingly, when the injector 12 is placed on projecting stem 98 of the energizing unit 92 with the stem 28 in its position seen in FIG. 3, the stem 28 at portion 28a enters the energizing sear assembly 100, depresses plug member 106 allowing the balls 104 to move inward, and the sear member 110 to move downward aligning ridge 110a with these balls. In this way, the stem 28 at portion 28a (i.e., the male portion of the energizing sear) is captured by ball members 104 in the stem 98. As the ball members 104 enter the groove 88, the cup-like sear member 110 moves downwardly to engage shoulder 110b on step 98a. In order to accomplish this engagement of the injector 12 on the unit 92, the user will have to exert a small downward force, pushing the stem 28 into the sear assembly 100 against the pre-load of spring 108.

Further considering FIGS. 4 and 4b, it is seen that the energizing unit 92 includes an electric motor unit 112, with an integral gear-head portion 112a, providing a great speed reduction and torque increase for the motor unit. A gear 114 is driven by the motor unit 112, and drivingly engages a gear 116 carried by and in driving engagement with a jack screw member 118. This jack screw 118 is journaled between a lower bearing unit 120 and an upper bearing unit 122, which also serves as a thrust bearing for the jack screw 118. Threadably carried on the jack screw member 118 is a nut plate member 124 to which a pair of tie rods 126 are secured. These tie rods extend upwardly through respective apertures 128 in a partition of the housing 94 supporting the bearing 122, and engage a pull plate member 130. This pull plate member 130 is coupled to a tubular stem 132 extending upward to couple with the stem member 98 and which carries female sear assembly 100.

Immediately above the pull plate member 130, stem 132 carries a plate-like limit switch actuating member 134. Similarly, next to the lower extent of the stem 98, the stem 132 also carries another plate-like limit switch actuating member 136. Carried by the housing 94 between the members 134 and 136 is a reversing limit switch 138 having an actuating arm 138a. Also carried on housing 94 is a microswitch 140 having an externally exposed actuating button 140a disposed to be engaged by the housing 16 of the injector 12 when this is seated on stem 98 and about in engagement with the abutment 96. Housing 94 also carries a limit switch 142 engaged by limit member 136 in its upper position as shown in FIG. 4, and a connector 144 by which electrical power can be supplied to the energizing unit 92. For example, the unit 92 is preferable designed to operate from low-voltage AC or DC power provided by a transformer (or transformer/rectifier) unit (not shown) operated from line power.

Viewing FIG. 4b, it is seen that the reversing switch 138 is double-pole, double-throw, and that when in the position depicted in FIG. 4 closes contacts "a" to contacts "b" to operate the motor 112 in a forward direction. The switch 142 shuts off power to the motor 112 when it is actuated by member 136 as seen in FIG. 4, but when the switch 140 is depressed at button 140a by the injector 12 being placed on stem 98, the motor 112 is momentarily powered via this switch. Powering of the motor 112 causes its operation in a forward direction so that the nut member 124, tie rods 126, pull plate member 130, and stem 132 connected to stem 98 are all pulled downwardly relative to the housing 94. Thus, the stem 98 retracts into the housing 94, and stem 128 is pulled along because of the connection at sear assembly 90. Once the stem 132 is moved downwardly slightly from its position seen in FIG. 4, the switch 142 provides power to operate the motor 112.

As the motor 112 operates and pulls stems 98 and 132 downwardly, the motion of stem 98 will at some time be great enough that the stem 28 moves from its position seen in FIG. 3 back to its position of FIG. 2. When this happens, the balls 58 will engage into groove 28d, but will not retain the stem 28 at this position because this stem is forced to move along with stem 98. In other words, the stem 28 is provided with some over-travel movement by elongation of groove 28d. Further, as the motor 112 operates and pulls stems 132 and 98 downwardly via operation of jack screw 118, a push rod member 146 which is slidably received in the bore of tubular stem 132 and at its lower end rests upon the partition 148 engages at its upper end with a depending stem 110c of the trigger member 110. Consequently, the trigger member 110 is moved relatively upwardly, and releases the balls 104 from groove 88, freeing the stem 28 of the injector 12. This release of the stem will be accompanied by a slight "pop" sound caused by the engagement of stem 28 at groove 28a with the balls 58. The balls 58 in this case will retain the stem 28, so that the injector is maintained in its energized or cocked position seen in FIG. 2.

Next, as the stems 132 and 98 are moved a short additional distance downwardly, the limit member 136 engages switch 138 to open the connection of contacts "a" to contacts "b", and close the connection of contacts "a" to contacts "c". This change of connections at the switch 138 reverses the direction of operation of motor 112. During this reversed-direction of operation of the motor 112, the jack screw 118 raises the stem 98 by operation of tie rods 126, etc., and power to the motor is provided by switch 142 because the injector 112 is not longer being held down on abutment 96. In fact, the injector 12 can be removed from the unit 92 as soon as the sear assembly 100 releases the stem 28. When the stem 98 reaches its upper position seen in FIG. 4, the limit member 136 again engages switch 142 and shuts off power to the motor 112. The motor stops because switch 140 is no longer being held closed.

In view of the above, it is seen that the injector 12 is pre-energized for its next use shortly after a user places it on the energizer unit 92. Understandably, the user will install a new or cleaned cartridge 14 on the injector, having pre-filled this cartridge with medication for the next injection to be given.

Considering now FIG. 6 in additional detail, it is seen that the injection cartridge 14 is in this Figure indicated with numeral 14'. The cartridge 14' seen in FIG. 6 is the same in all respects except one, as the cartridge 14 seen in the earlier drawing Figures. Thus, the same reference numerals used above are used in FIG. 6. Viewing FIG. 6, it is seen that the injection cartridge 14' includes in addition to the features of the cartridge 14 depicted and described above, a pair of diametrically opposed lugs 44 which are disposed near the forward end of the injection cartridge 14'. The lugs 44 are disposed on opposite sides of the injection orifice 42, and allow an authorized user of the injection device 10 to refill the injection cartridge 14 by interfacing this cartridge via the lugs 44 with a pressurization device that will force medication into the cartridge 14' via the injection orifice 42. Thus, although the piston 34 of cartridge 14' has a bluff rear surface 34a just like the piston of cartridge 14, so that the piston 34 once it is moved forward to its position of FIG. 3 cannot be grasped from the surface 34a, and cannot be in that way returned to its position of FIG. 2, cartridge 14' allows the piston 34 to be retracted to its position seen in FIG. 2 by application of pressurized medication. As the pressurized medication is injected into the cartridge 14' via the injection orifice 42, the dose of medication is noted by use of gradations 14a provided along the side of this cartridge.

FIGS. 7 and 8 depict an alternative embodiment of an energizing unit 150 for use with the injector 12 described above. The energizing unit 150 seen in FIGS. 7 and 8 does not use a motor or other power source, but instead depends upon force and displacement provided by a human stepping on a pedal 152 of the unit. For this purpose, the unit 150 includes a base 154 received on a floor, for example, and a column 156 extending upwardly from this base. Near its upper extent, the column 156 carries a stem (not shown) which is similar to stem 98 and carries the female portion 100 of an energizing sear assembly 90. The column 156 defines an abutment 158 at its upper extent against which the injector 12 is abutted when placed over the stem of this unit preparatory to cocking the injector 12.

FIG. 8 shows that the unit 150 includes a tension element 160 (i.e., a flexible cable in this case) secured to and extending from the pedal 152 downwardly around a sheave 162 formed by a rotational sleeve received around a cross shaft 164, and extending upwardly inside of the column to connect with the energizing stem (i.e., the stem like stem 98 with sear assembly 100). In this way, injection units 12 may quickly and easily be cocked preparatory to their use in giving injections. Further, the foot-powered unit 150 avoids the necessity for electrical power, and my be used under primitive or mobile-treatment conditions. For example, a military field hospital unit may use a unit 150 and injectors 12 in the field.

An advantage of the present invention resides in its provision of an injector that is simpler in its construction, smaller in size, and lighter than would be the case were it required to also include some mechanism for cocking or re-energizing the spring of this injector. All that is required to be included in the injector 12 is an interface portion of the energizing sear assembly. That is, the aft end of stem 28 includes the groove 88 for interface with the sear assembly 100, and the housing 16 defines an abutment for reacting the full force generated by jack screw 118, or delivered by the cable 160. In clinical situation in which medical personnel give a large number of injections every day, such personnel may benefit greatly by the speed of preparation of the injector 12, and the absence of any need for them to cock this injector when the unit 94 is utilized. Even when a foot-powered cocking device, like that shown in FIGS. 7 and 8 is utilized, the speed of preparation of an injector 12 is very quick. This speed of preparation of an injector is complemented by the speed and ease of giving an injection using the injector 12. That is, the user simply presses the cartridge 14 of an injector 12 to the skin, pulls the safety trigger 18, and pushes a little more to slide the triggers 20 forward. The injector 12 discharges in a fraction of a second, injecting the medication in an almost painless jet injection process. Next the user either removes and discards the cartridge, or places this in a container for cleaning and reuse with the same patient. Placing the injector 12 back on the unit 92 quickly re-cocks it and makes it ready for another injection. Alternatively, a human-powered re-cocking device like that shown in FIGS. 7 and 8 may be used.

While the invention has been depicted and described by reference to two particularly preferred embodiments of the invention, such reference does not imply a limitation on the invention, and no such limitation is to be inferred. The invention is capable of considerable variation and alteration in its embodiments without departing from the scope of this invention. For example, a human-powered cocking device for the injector depicted and described above can easily be envisioned which is table-top mounted, and uses hand power to cock the injector, rather than being foot-powered as is depicted in FIGS. 7 and 8 of this disclosure. Accordingly, the invention is intended to be limited only by the spirit and scope of the appended claims, giving cognizance to equivalents in all respects.

What is claimed is:

1. A needle-less hypodermic jet injection system including a hand-held injection unit and a separate energizing unit, said hand-held injection unit being configured for administering a liquid medication in the form of a hypodermic jet injection, said injection system comprising:

a hand-held injection unit including means for mounting thereto an injection cartridge with medication cylinder, injection nozzle, and injection piston; said hand-held injection unit also including an injection ram for driving said injection piston, a power unit which is pre-energized prior to each injection to store injection energy to be applied to the injection ram; and a trigger mechanism allowing the energy stored in the power unit to be released and applied in driving the injection ram to cause the medication to be ejected via said injection nozzle forming the hypodermic injection jet;

said trigger mechanism including an outer trigger sleeve outwardly adapted to be manually grasped and movable axially along a portion of said hand-held injection unit, and forward movement of said outer trigger sleeve being effective to release the energy stored in the power unit; and a separate energizing unit with which the hand-held injection unit interfaces to be energized to store injection energy so as to subsequently power an injection;

wherein said outer trigger sleeve outwardly carries a pair of diametrically opposed trigger members, each of said diametrically opposed trigger members extending outwardly relative to said hand-held injection unit, and said trigger members providing manual purchase for effecting forward movement of said outer trigger sleeve to release the energy stored in said power unit; and wherein one of said pair of diametrically opposed trigger members pivotally carrying a release member, and said release member being pivotal between a first position interposing a safety member between said trigger sleeve and a stop member, and said safety member in a second position withdrawing said safety member from interposition between said trigger sleeve and said stop member to allow said trigger sleeve to be manually moved forward along said hand-held injection unit.

2. The injection system of claim 1 wherein said energizing unit includes a power drive, and means causing operation of said power drive upon interface of said hand-held injection unit with said energizing unit to provide stored energy in said power unit.

3. The injection system of claim 1 wherein said energizing unit includes a means for receiving force and displacement from a human while said hand-held injection unit is interfaced with said energizing unit, and for applying this force and displacement as power stored in said power unit.

4. The injection system of claim 1 wherein each of said hand-held injection unit and said energizing unit each define a respective one component of a pair of cooperative force transmitting structures, which cooperative components engage one another in force transmitting relationship upon interface of said hand-held injection unit with said energizing unit, said cooperative force transmitting structures transmitting energy from said energizing unit to said hand-held injection unit by transmission of an applied force acting over a certain distance.

5. The injection system of claim 4 wherein said hand-held injection unit includes an axially movable injector stem having a ram portion for abutting said injection piston, said injector stem being movable axially between a first position in which said power unit is discharged of energy and a second position in which said power unit stores energy for driving said ram portion to power a hypodermic jet injection, and said injector stem further includes an opposite end portion defining a respective one of said pair of force-transmitting cooperative structures.

6. The injection system of claim 5 wherein said energizing unit includes a stem which is forcefully movable, and said stem of said energizing unit having a clutch for engaging said end portion of said injector stem in force transmitting relationship, said clutch defining the other of said pair of force-transmitting cooperative structures.

7. The injection system of claim 6 wherein said end portion of said injector stem defines a circumferential groove, and said clutch of said energizing unit includes an axially extending bore for receiving said end portion and circumferential groove thereof, said clutch including at least one member which is receivable into said groove of said injector stem to couple said injector stem and clutch to transmit force between said energizing unit and said hand-held injection unit.

8. The injection system of claim 7 wherein said clutch includes a ball-clutch mechanism, and said at least one member includes a ball carried in said clutch and receivable into said groove of said injector stem to releasably lock the latter to said clutch during force transmission.

9. The injection system of claim 5 wherein said power unit includes a coil compression spring, said coil compression spring engaging said injector stem of said hand-held injection unit to forcefully drive said stem.

10. The injection system of claim 9 wherein said hand-held injection unit trigger mechanism includes a sear for engaging and holding said injector stem of said hand-held injection unit in an axial position storing energy in said coil compression spring.

11. The injection system of claim 10 wherein said trigger mechanism sear includes a second groove defined on said injector stem, and a second ball clutch carried in said hand-held injection unit and circumscribing said injector stem, said second ball clutch having at least one ball member releasably engageable into said second groove of said injector stem to retain the latter in said second position.

12. A needle-less hypodermic jet injection system including an energizing unit, and a separate hand-held injection unit, said hand-held injection unit being for use with an injection cartridge having a cylinder for receiving liquid medication, an orifice for forming the liquid into a high-velocity hypodermic injection jet, and an injection piston sealingly movable in said cylinder to displace said liquid medication via said orifice; said needle-less injection system comprising:

a hand-held injection unit including an injection ram abutting with said injection piston of said injection cartridge to forcefully drive the latter to form an injection jet of liquid medication held in said cylinder of said cartridge, said hand-held injection unit including a power unit which is energized prior to each injection; and a trigger mechanism allowing the energy stored in the power unit to be released and applied in driving the injection ram to cause the formation of said hypodermic injection jet;

said trigger mechanism including an outer trigger sleeve outwardly adapted to be manually grasped and movable axially along a portion of said hand-held injection unit, and forward movement of said outer trigger sleeve being effective to release the energy stored in the power unit; and a separate energizing unit with which the hand-held injection unit interfaces prior to each injection to be energized by the application of mechanical force and displacement acting over a distance to store energy in said power unit with which to power an injection;

wherein said outer trigger sleeve outwardly carries a pair of diametrically opposed trigger members, each of said diametrically opposed trigger members extending outwardly relative to said hand-held injection unit, and said trigger members providing manual purchase for effecting forward movement of said outer trigger sleeve to release the energy stored in said power unit; and wherein one of said pair of diametrically opposed trigger members pivotally carrying a release member, and said release member being pivotal between a first position interposing a safety member between said trigger sleeve and a stop member, and said safety member in a second position withdrawing said safety member from interposition between said trigger sleeve and said stop member to allow said trigger sleeve to be manually moved forward along said hand-held injection unit.

13. The needle-less injection system of claim 12 wherein said power unit of said hand-held injection unit includes a resilient member, said hand-held injection unit further including an injection stem which is axially movable and includes a ram portion for engaging said injection piston, said injection stem being movable axially between a first position in which said resilient member of said power unit is discharged of energy and a second position in which said power unit stores energy for driving said ram portion to power a hypodermic jet injection, and said injection stem of said hand-held injector further includes an opposite end portion defining a respective one of a pair of force-transmitting cooperative structures engageable to transmit mechanical power via said injection stem into said resilient member.

14. The needle-less injection system of claim 13 wherein said energizing unit includes a means for receiving force and displacement from a human, and the other one of a pair of force transmitting cooperative structures is engageable with said injection stem to transmit this force and displacement as power to be stored in said resilient member of said power unit.

15. The needle-free injection system of claim 14 wherein said opposite end portion of said injection stem includes an engagement surface for receiving force from said energizing unit, said energizing unit having a clutch for engaging said opposite end portion of said injector stem in force transmitting relationship, and said clutch defining the other of said pair of force transmitting cooperative structures.

16. The needle-less injection system of claim 15 wherein said opposite end portion of said injection stem defines a circumferential groove with a shoulder which forms said engagement surface, and said clutch of said energizing unit includes an axially extending bore for receiving said opposite end portion and circtunferential groove thereof, said clutch including at least one member which is receivable into said groove or said injection stem to engage said engagement surface so as to releasably couple said stem and clutch to transmit force between said energizing unit and said hand-held injection unit.

17. The injection system of claim 13 wherein said trigger mechanism sear includes a second groove defined on said injection stem, and a ball clutch carried in said hand-held injection unit and circumscribing said injection stem, said ball clutch having at least one ball member releasably engageable into said second groove of said injection stem to retain the latter in said second position.

18. The needle-less injection system of claim 12 wherein said power unit includes a coil compression spring, said coil compression spring engaging said injection stem of said hand-held injection unit to forcefully drive said stem.

19. The needle-less injection system of claim 12 wherein said injector trigger mechanism includes a trigger mechanism sear for engaging and holding said injection stem of said injector in an axial position storing energy in said coil compression spring.

20. A method of effecting a needle-less hypodermic jet injection using an injection cartridge having a cylinder for receiving liquid medication, an orifice for forming the liquid into a high-velocity hypodermic injection jet, and an injection piston movable sealingly in said cylinder to displace said liquid medication via said orifice; said method including steps of:

providing a hand-held injection unit including an injection ram engageable with said injection piston of said injection cartridge to forcefully drive the latter to form an injection jet of liquid medication held in said cylinder of said cartridge, configuring said hand-held injection unit to include a power unit which is energized with mechanical energy prior to each injection; and a trigger mechanism allowing the energy stored in the power unit to be released and applied in driving the injection ram to cause the formation of said hypodermic injection jet; providing said trigger mechanism to include an outer trigger sleeve, outwardly adapting the trigger sleeve to be manually grasped and movable axially along a portion of the hand-held injection unit, and providing for forward movement of the outer trigger sleeve to be effective to release the energy stored in the power unit; and utilizing a separate energizing unit to interface with the hand-held injection unit prior to each injection in order to re-energize the hand-held injection unit by the application of mechanical power to store energy in said power unit;

further including the steps of providing the outer trigger sleeve with a pair of diametrically opposed trigger members, extending each of the diametrically opposed trigger members outwardly on the trigger sleeve relative to the hand-held injection unit, and providing for the pair of trigger members to provide manual purchase for effecting forward movement of the outer trigger sleeve to release the energy stored in the power unit; and further including the steps of providing for one of the pair of diametrically opposed trigger members to pivotally carry a release member, providing the release member to be pivotal between a first position interposing a safety member between the trigger sleeve and a stop member to prevent forward movement of the trigger sleeve, and providing for the safety member to in a second position withdraw the safety member from interposition between the trigger sleeve and the stop member allowing the trigger sleeve to be manually moved forward along the hand-held injection unit.

21. The needle-less injection method of claim 20 further including the step of: providing means for receiving force and displacement from a human, and configuring said energizing unit to receive this force and displacement and to apply the same as power to be stored in said power unit while said hand-held injection unit is interfaced with said energizing unit.

22. The needle-free injection method of claim 20 further including the step of: providing a power drive unit, and interfacing said power drive unit with said hand-held injection unit to store energy in said power unit.

23. The needle-free injection method of claim 22 in which said power drive unit includes an electric motor for providing mechanical energy to be stored in said power unit.

* * * * *